United States Patent [19]

MacIntosh

[11] Patent Number: 5,314,698
[45] Date of Patent: May 24, 1994

[54] ISOLATION OF BRUSH BORDER MEMBRANE VESICLES FROM WHOLE INSECT LARVAE

[75] Inventor: Susan C. MacIntosh, Woodland, Calif.

[73] Assignee: Novo Nordisk A/S, Bagsvaerd, Denmark

[21] Appl. No.: 846,265

[22] Filed: Feb. 7, 1992

[51] Int. Cl.$^5$ .............................................. A61K 35/64
[52] U.S. Cl. .................................... 424/538; 424/551
[58] Field of Search ................................ 424/551, 538

[56] References Cited

PUBLICATIONS

Sabolic et al., Biochim. Biophys. Acta 772:140–148 (1984).
Kinsella et al., Biochim. Biophys. Acta 552:468–477 (1979).
Yakymyshyn et al. Biochim. Biophys. Acta 690:269–281 (1982).
Wolfersberger et al., Comp. Biochem. Phys. 86A:3-01–08 (1987).

*Primary Examiner*—Douglas W. Robinson
*Assistant Examiner*—Jean C. Witz
*Attorney, Agent, or Firm*—Steve T. Zelson; Elias J. Lambiris

[57] ABSTRACT

The present invention relates to an improved method for isolating brush border membranes from insects. The method can be used to isolate brush border membranes from small insects.

11 Claims, No Drawings

ISOLATION OF BRUSH BORDER MEMBRANE VESICLES FROM WHOLE INSECT LARVAE

BACKGROUND OF THE INVENTION

*Bacillus thuringiensis* has been used as a microbial insecticide for over twenty years. Its insecticidal activity resides in proteinaceous crystalline inclusions which are produced during sporulation. When ingested by susceptible insect larvae, they are dissolved in the intestinal lumen and proteolytically processed to active toxins which cause lysis of midgut epithelial cells.

Brush border membrane vesicles (BBMV) from larval midgut are very useful in analyzing the mode of action of insecticidal bacterial endotoxins. Indeed, a receptor binding assay which measures the binding of the endotoxin to brush border membrane vesicles has been developed.

For example, Hofmann et al. reported the binding of endotoxin of *B. thuringiensis* subspecies thuringiensis to brush border membrane vesicles of *Pieris brassicae* larval midgut C. Hofmann, P. Luthy, R. Hutter and V. Pliska, *Eur. J. Biochem.* 173, pp. 85-91 (1988). See also B. H. Knowles and D. J. Ellar, *J. Cell Sci.* 83, pp. 89-101 (1986); C. Hofmann, H. Vanderbruggen, H. Hofte, J. Van Rie, S. Jansens and H. Van Mellaert, *Proc. Natl. Acad. Sci. USA* 85, pp. 7844-48 (1988); J. Van Rie, S. Jansens, H. Hofte, D. Degheele and H. Van Mellaert, *Appl. Environ. Microbiol.* 56, pp. 1378-85 (1990); M. G. Wolfersberger, *Experientia* 46, pp. 475-77 (1990); J. Van Rie, W. H. McGaughey, D. E. Johnson, B. D. Barnett and H. Van Mellaert, *Science* 247, pp. 72-74 (1990); and S. C. MacIntosh, T. B. Stone, R. S. Jokerst and R. L. Fuchs, *Proc. Natl. Acad. Sci. USA* 88, pp. 8930-33 (1991).

Brush border membrane vesicles have also been utilized for studies of cotransport mechanisms in lepidopteran gut. See, e.g., B. Giordana, V. F. Sacchi, P. Parenti and G. M. Hanozet, *Am. J. Physiol.* 257, pp. R494-R500 (1989); G. M. Hanozet, B. Giordana and V. F. Sacchi, *Biochem. Biophys. Acta* 596, pp. 481-86 (1980); M. Wolfersberger, P. Luthy, A. Maurer, P. Parenti, V. F. Sacchi, B. Giordana and G. M. Hanozet, *Comp. Biochem. Physiol.* 86A, pp. 301-08 (1987); and V. F. Sacchi, P. Parent, G. M. Hanozet, B. Giordana, P. Luthy and M. G. Wolfersberger, *FEBS Lett.* 3904, pp. 213-18 (1986).

However, research into the mode-of-action of stomach active insecticides and studies of cotransport mechanisms in lepidopteran gut is presently limited. The experiments require large amounts of brush border membrane vesicles which are not widely available partly due to the difficulty in isolating them from insect midguts. The current method for isolating brush border membrane vesicles requires dissecting individual insect larvae to obtain the midgut tissue. This is very time consuming and labor intensive.

Moreover, most biochemical studies of insect midgut function and mode-of-action have focused on lepidopteran systems using relatively large species, e.g., *Manduca sexta*, *Heliocoverpa virescens* and *Spodoptera fruqiperda*. Comparatively little research has been done on either coleoptera or diptera, partially due to the difficulty in isolating brush border membrane vesicles from small insects. Large insects allow for relatively easy dissection with substantial yield of brush border membrane vesicles per insect, but most lepidopterans are much smaller. On the other hand, small lepidopteran larvae are very difficult to dissect, requiring large number of larvae for isolating a relatively small quantity of brush border membrane vesicles.

A diversity of insect model systems will enhance the overall understanding of *Bacillus thuringiensis* mode-of-action and, therefore, enhance our ability to improve these insecticides.

It is therefore an object of the present invention to provide an improved method for isolating brush border membrane vesicles from insect larvae which produces large quantities of vesicles in a short time.

It is another object of the present invention to provide a method for isolating brush border membrane vesicles from small insect larvae.

SUMMARY OF THE INVENTION

The present invention relates to an improved method for isolating brush border membrane vesicles from whole insect larvae comprising
  (a) blending whole insect larvae in a buffer solution which does not have metal binding characteristics;
  (b) removing the insect larvae exoskeleton from the blended solution; and
  (c) isolating the brush border membranes from the blended solution after removal of said insect larvae exoskeleton whereby the brush border membranes form vesicles.

DETAILED DESCRIPTION OF THE INVENTION

The present invention relates to a method for isolating brush border membrane vesicles from insect larvae. The method according to the present invention is much more efficient than the prior art methods. In addition, the method according to the present invention can isolate brush border membrane vesicles from small insects.

The method according to the present invention comprises
  (a) blending whole insect larvae in a buffer solution which does not have metal binding characteristics;
  (b) removing the insect larvae exoskeleton from the blended solution; and
  (c) isolating the brush border membranes from the blended solution after removal of said insect larvae exoskeleton whereby the brush border membranes form vesicles.

The first step, i.e., the blending of whole insect larvae, may be done by placing the whole insect larvae in a beaker containing a buffer solution which does not have metal binding characteristics and then homogenizing the mixture with a polytron mixer until the insects are pulverized. Preferably, the buffer solution has a pH of about 6 to about 9, more preferably, a pH of about 6.5 to about 8.5, and most preferably, a pH of about 7.5.

A suitable buffer for the blending step is a solution of mannitol, ethyleneglycol bis(alpha-aminoethyl ether)-N,N'-tetraacetic acid and tris-(hydroxymethyl) aminomethane (tris)-HCl (MET). Other suitable buffers include the above-mentioned solution, wherein tris-(hydroxymethyl) aminomethane (tris)-HCl is replaced by (1) 4-(2-hydroxyethyl)-piperazine-1-ethanesulfonic acid (HEPES), (2) N[tris(hydroxymethyl)methyl]-2-aminoethanesulfonic acid (TES), (3) 3-[N-bis(hydroxyethyl)amino]-2-hydroxypropanesulfonic acid (DIPSO) or (4) piperazine-N,N-bis(2-hydroxy)propanesulfonic acid (POPSO). Preferably, the buffer is 300 mM mannitol, 5 mM ethyleneglycol bis(alpha-aminoethyl ether)-N,N'- tetraacetic acid and 17 mM tris-(hydroxymethyl) aminomethane (tris)-HCl.

Persons of skill in the art will appreciate that whole insect larvae may be blended by other techniques.

The exoskeleton (tough body parts) can be removed from the mixture of whole insect larvae in many ways. For example, the exoskeleton may be removed by centrifugation at 1000×g for 10 minutes and/or by filtration through a double layer of cheesecloth.

The brush border membrane vesicles may be isolated according to the following steps:

(a) blending the mixture of whole insect larvae without the exoskeleton to form a homogenate;

(b) mixing the homogenate with a metal salt and incubating for a sufficient amount of time to precipitate said brush border membrane vesicles;

(c) low speed centrifugation of the homogenate containing the precipitate to form a supernatant containing said brush border membrane vesicles;

(d) high speed centrifugation of the supernatant containing said brush border membrane vesicles to form a pellet of said brush border membrane vesicles; and (e) suspension of the pellet of said brush border membrane vesicles in a homogenate.

This isolation procedure takes advantage of the highly charged nature of the brush border membranes due to the proteins on their surface. The other cell membranes in insect tissues are less charged and, therefore, are not precipitated by the metal salt. Hence, the metal salt effectively separates the brush border membranes from the other gut cell membranes. Preferably, the metal salt is a divalent salt, e.g. $MgCl_2$ or $CaCl_2$, most preferably, $MgCl_2$.

After precipitating the brush border membranes, the homogenate containing the precipitate is centrifuged at a low speed, i.e., between about 2,000 and about 3,000×g, to form a supernatant containing the brush border membrane vesicles.

The supernatant is then centrifuged at a high speed, i.e., at least about 30,000×g, to form a pellet of said brush border membrane vesicles.

The pellet of said brush border vesicles is then suspended in a homogenate. Suitable homogenates include the above-mentioned buffers used in the blending step. Preferably, the homogenate is 300 mM mannitol, 5 mM ethyleneglycol bis(alpha-aminoethyl ether)-N,N'-tetraacetic acid and 17 mM tris-(hydroxymethyl) aminomethane (tris)-HCl.

Persons of skill in the art will appreciate that other techniques can be used to isolate the brush border membrane vesicles.

The brush border membrane vesicles may be further purified by repeating steps (b)–(e) of the isolation procedure. Preferably, the brush border membrane vesicles go through this purification cycle at least two times in order to enhance the specific activity of the marker enzymes.

The method according to the present invention can be used to isolate brush border membrane vesicles from all lepidoptera, coleoptera and diptera. Preferably, the insect larvae are small lepidoptera. Most preferred insect larvae are diamondback moth.

The present invention will now be described by the following non-limiting example.

EXAMPLE

Materials & Methods

Reagents

All chemicals were reagent grade and purchased from Sigma Chemical Co. (St. Louis, Mo.).

Insect Colony Description

A colony was initiated from eggs and 800 pupae received 9/90 from Yakima Agricultural Research Lab, U.S.D.A., ARS, Yakima, Wash. (Duane Biever).

Isolation of Brush Border Membrane Vesicles

1. Prior Art Method

Fifth instar diamondback moth (DBM) larvae were placed on a petri dish filled with ice. With the aid of a dissecting microscope, the head and tail were grasped with fine tweezers. The gut was separated by carefully pulling the gut from the cuticle, which was discarded. The number of larvae was recorded. The gut was placed in an ice cold solution of 300 mM mannitol, 5 mM ethyleneglycol bis(alpha-aminoethyl ether)-N,N'-tetracetic acid (EGTA), 17 mM tris(hydroxymethyl) aminomethane (Tris)-HCL, pH 7.5. The remainder of the purification method was as described in M. G. Wolfersberger, P. Luthy, A. Maurer, P. Parenti, V. F. Sacchi, B. Giordana and G. M. Hanozet, *Comp. Biochem. Physiol.* 86A, pp. 301–08 (1987).

2. Method according to the Present Invention

Fifth instar DBM larvae were counted, weighed and placed in a 50 ml beaker with a minimal volume of ice cold MET buffer (usually 2 ml/100 insects). This mixture was homogenized with a polytron mixer until all insects were pulverized. Centrifugation at a speed of 1000×g followed by filtration through a double layer of cheesecloth efficiently removed the intact pieces of exoskeleton. The supernate was homogenized and mixed with an equal volume of 24 mM magnesium chloride. The remainder of the purification method was as described in M. G. Wolfersberger, P. Luthy, A. Maurer, P. Parenti, V. F. Sacchi, B. Giordana and G. M. Hanozet, *Comp. Biochem. Physiol.* 86A, pp. 301–08 (1987). For some preparations, a portion of the brush border membrane vesicles were subjected to a third purification cycle.

Purified brush border membrane vesicle preparations were dispensed in vials, quickly frozen in liquid nitrogen, and stored at −80° C. for up to 6 months.

Enzyme Assays

The integrity of brush border membrane vesicles is measured by cell bound enzymes, i.e., leucine amino peptidase, glutamyl transferase and alkaline phosphatase. The specific activity, defined as the enzyme activity divided by the protein concentration of a given sample, provides the relative purity and amount of brush border membrane vesicles.

Enzymatic assays were performed in triplicate on each homogenate and brush border membrane vesicle preparation. All assays were done with excess substrate, and the measured product increased linearly with the enzyme concentration. Calculations of specific activity were only delineated from time points during the linear portion of each enzymatic reaction. Alkaline phosphatase (EC 3.1.3.1) activity was measured for the fresh samples using the method of O. H. Lowry, N. R. Roberts, M. L. Wu, W. S. Hixon and E. J. Crawford, *J. Biol. Chem.* 207, pp. 19-37 (1954). Aminopeptidase (EC 3.4.11.2) activity was assayed according to the method of H. Tuppy, U. Weisbauer and E. Wintersberger, *Z. Physiol. Chem.* 329, pp. 278-88 (1962) and gamma-glutamyl transferase (EC 2.3.2.2) activity was measured using the method described in S. B. Rosalki and D. Tarlow, *Clin. Chem.* 20, pp. 1121-24 (1974). The latter two enzymes were stable upon freezing, and therefore, the assay was performed on frozen samples. Alkaline phosphatase was not measured on preparations from dissected midgut tissue. All enzymes were assayed kinetically on a Shimadzu UV-260 spectrophotometer or adapted to a microliter plate and read on a BioRad Model 3550 Microplate reader using Kinetic Collector analysis software on a Macintosh computer.

Protein Determination

Protein concentrations were determined by the method of M. M. Bradford, *Anal. Biochem.* 72, pp. 248-54 (1976) using bovine serum albumin as a standard.

Results

On three different days, brush border membrane vesicles were isolated from both isolated guts and whole DBM larvae. In the preparations isolated according to the method of the present invention, the total protein was doubled (data not shown). Enzyme analysis was performed on both the initial homogenate and the final brush border membrane vesicles (Table 1). As shown in Table 1, there was an increase in protein and a reduction in specific activity of two marker enzymes by approximately 1.5-1.7 fold in the method of the present invention. Since the total yield of enzyme activity was roughly the same between the two methods, the addition of another purification cycle was evaluated.

The pellet from the second precipitation-differential centrifugation cycle was resuspended in MET and divided into two equal portions. One portion was subjected to an additional precipitation-differential centrifugation cycle. This additional cycle decreased the total protein by about 2 fold without a loss of enzymatic activity (data not shown), thereby enhancing the specific activity by 2-3 fold (Table 2). The specific activity of these triple preparations now was higher than the brush border membrane vesicles isolated from gut tissue by 1.3-2.7 fold (Tables 1 and 2).

TABLE 1

Enzymatic activities of subcellular fractions from midgut and whole *P. xylostella* larvae

| Tissue | Source | Leucine[a] Aminopeptidase | γ-Glutamyl[a] Transferase |
|---|---|---|---|
| Homogenate | midgut | 751 ± 87 | 21.7 ± 5.9 |
| BBMV | midgut | 3540 ± 640 | 68.1 ± 31.6 |
| Homogenate | whole[b] | 235 ± 68 | 5.7 ± 1.2 |
| BBMV | whole | 2132 ± 62 | 46.0 ± 14.9 |

[a]Specific activity expressed as units of nmole min$^{-1}$ mg protein$^{-1}$.
[b]From whole larvae.

TABLE 2

Enzymatic activities of subcellular fractions from whole *P. xylostella* larvae

| Tissue | Alkaline[a] Phosphatase | Leucine[b] Aminopeptidase | γ-Glutamyl[b] Transferase |
|---|---|---|---|
| Homogenate | 31 ± 4 | 248 ± 14 | 7 ± 1 |
| BBMV-2 ppt | 147 ± 18 | 2151 ± 322 | 61 ± 12 |
| BBMV-3 ppt | 447 ± 36 | 4702 ± 515 | 186 ± 53 |

[a]Specific activity expressed as units of μmole min$^{-1}$ mg protein$^{-1}$.
[b]Specific activity expressed as units of nmole min$^{-1}$ mg protein$^{-1}$.

I claim:
1. A method for isolating brush border membranes from insect larvae comprising:
   (a) blending whole insect larvae in a buffer solution which does not have metal binding characteristics;
   (b) removing the insect larvae exoskeleton from the blended solution;
   (c) homogenizing the blended solution containing the whole insect larvae without the exoskeleton to form a homogenate;
   (d) mixing the homogenate with a metal salt to form a mixture and incubating for a sufficient amount of time to precipitate the brush border membranes;
   (e) centrifuging the mixture a speed between about 2,000 and about 3,000×g to form a supernatant containing said brush border membranes; and
   (f) centrifuging the supernatant containing said brush border membranes at least 30,000×g to form a pellet of said brush border membranes.
2. The method according to claim 1, wherein the metal salt is a divalent salt.
3. The method according to claim 2, wherein the metal salt is MgCl$_2$ or CaCl$_2$.
4. The method according to claim 1, wherein the buffer solution has a pH of about 6 to about 9.
5. The method according to claim 4, wherein the buffered solution has a pH of about 6.5 to about 8.5.
6. The method according to claim 5, wherein the buffer solution has a pH of about 7.5.
7. The method according to claim 1, wherein the insect larvae are lepidoptera, coleoptera or diptera.
8. The method according to claim 7, wherein the insect larvae are lepidoptera.
9. The method according to claim 8, wherein the insect larvae are diamondback moths.
10. The method according to claim 1, wherein the purification of the brush border membranes comprises:
   (a) homogenizing the pellet of said brush border membranes in a second homogenate;
   (b) mixing the second homogenate containing the pellet with a metal salt to form a second mixture and incubating for a sufficient amount of time to precipitate the brush border membranes;
   (c) centrifuging the second mixture at a speed between about 2,000 and about 3,000×g to form a second supernatant containing said brush border membranes; and
   (d) centrifuging the second supernatant at at least 30,000×g containing said brush border membranes to form a second pellet of said brush border membranes.
11. The method according to claim 10, further comprising:
   (i) homogenizing the second pellet of said brush border membranes to form a third homogenate;
   (ii) mixing the third homogenate with a metal salt to form a third mixture and incubating for a sufficient amount of time to precipitate the brush border membranes;
   (iii) centrifuging the third mixture at a speed between about 2,000 and about 3,000×g to form a third supernatant containing said brush border membranes; and
   (iv) centrifuging the third supernatant containing said brush border membranes at at least 30,000×g to form a third pellet of said brush border membranes.

* * * * *